United States Patent
Ways et al.

(10) Patent No.: US 6,225,301 B1
(45) Date of Patent: May 1, 2001

(54) THERAPEUTIC TREATMENT FOR RENAL DYSFUNCTION

(75) Inventors: Douglas Kirk Ways, Indianapolis, IN (US); Richard Ernest Gilbert, Enocrine Unite, Austin Hospital, Studely Rd., Heidelberg 3084 (AU)

(73) Assignees: Eli Lilly and Company, Indianapolis, IN (US); Richard Ernest Gilbert, Heidelberg (AU)

( * ) Notice: Subject to any disclaimer, the term of this patent is extended or adjusted under 35 U.S.C. 154(b) by 0 days.

(21) Appl. No.: 09/253,718

(22) Filed: Feb. 22, 1999

Related U.S. Application Data
(60) Provisional application No. 60/076,852, filed on Mar. 5, 1998.

(51) Int. Cl.$^7$ .................................................. A61K 31/33
(52) U.S. Cl. .............................................................. 514/183
(58) Field of Search ................................................ 514/183

(56) References Cited

U.S. PATENT DOCUMENTS

| | | | |
|---|---|---|---|
| 5,057,614 | 10/1991 | Davis et al. | 548/466 |
| 5,481,003 | 1/1996 | Gillig et al. | 548/455 |
| 5,491,242 | 2/1996 | Gillig et al. | 548/455 |
| 5,545,636 | 8/1996 | Heath, Jr. et al. | 514/214 |
| 5,552,396 | 9/1996 | Heath, Jr. et al. | 514/183 |
| 5,559,228 | 9/1996 | Gillig et al. | 540/460 |
| 5,616,577 * | 4/1997 | Nambi et al. | 514/215 |
| 5,621,098 | 4/1997 | Heath, Jr. et al. | 540/472 |
| 5,674,862 | 10/1997 | Heath et al. | 514/183 |
| 5,698,578 | 12/1997 | Heath et al. | 514/410 |
| 5,710,145 | 1/1998 | Engel et al. | 514/183 |
| 5,780,461 | 7/1998 | Heath, Jr. et al. | 514/183 |

FOREIGN PATENT DOCUMENTS

| | | |
|---|---|---|
| 0 657 411 A1 | 6/1995 | (EP) . |
| 0 657 458 A1 | 6/1995 | (EP) . |
| 97 18809 | 5/1997 | (WO) . |

OTHER PUBLICATIONS

Wilkinson et al.. "Isoenzyme specificity of bisindolylmaleimides, selective inhibitors of protein kinase C" Biochem J. (1993) 294 pp. 335–337.

Hidehiro Ishii et al. "Amelioration of vascular dysfunctions in diabetic rats by an oral PKC beta inhibitor" Science 1996 272 (5262) pp. 728–731.

D. Koya et al. "Characterization of protein kinase C beta isoform activation on the gene expression of transforming growth factor–beta, extracellular matrix components, and prostanoids in the glomeruli of diabetic rats" Journal of Clinical Investigation (Jul. 1, 1997) 100 (1) pp. 115–126.

M.F. McCarty "A central role for protein kinase C overactivity in diabetic glomerulosclerosis: implications for prevention with antioxidants, fish oil, and ACE inhibitors." Medical Hypotheses, (Feb. 1998) 50 (2) pp. 155–165.

E.N. Wardle "How does hyperglycaemia predispose to diabetic nephropathy?" QJM, (Dec. 1996) 89 (12) pp. 943–951.

H. Ishii et al. "Protein kinase C activation and its role in the development of vascular complications in diabetes mellitus" Journal of Molecular Medicine, (Jan. 1998) 76 (1) pp. 21–31.

* cited by examiner

*Primary Examiner*—Kimberly Jordan
(74) *Attorney, Agent, or Firm*—Paul R. Darkes

(57) ABSTRACT

A method for treating renal dysfunctions is disclosed, particularly using the isozyme selective PKC inhibitor, (S)-3,4-[N, N'-1,1'-((2"-ethoxy)-3'"(O)-4'"-(N,N-dimethylamino)-butane)-bis-(3,3'-indolyl) ]-1(H)-pyrrole-2,5-dionehydrochloridesalt.

18 Claims, No Drawings

THERAPEUTIC TREATMENT FOR RENAL DYSFUNCTION

This application claims the benefit of co-pending provisional application Serial No. 60/076,852, filed Mar. 5, 1998, which is incorporated herein by reference.

BACKGROUND OF THE INVENTION

1. Field of the Invention

The present invention is broadly directed to a method for inhibiting intraglomerular hypertension, glomerulosclerosis, and glomerular-interstitial fibrosis, and especially such events associated with renal dysfunctions, e.g., acute and chronic renal failure. The present invention is particularly directed to the use of a particular class of isozyme selective Protein Kinase C (PKC) inhibitors for preventing and treating renal dysfunctions, e.g., renal insufficiency, acute and chronic renal failure, and complications associated with loss of renal function.

2. Description of Related Art

Over the past three decades, dialysis and transplantation have become effective treatment modalities in prolonging the life of patients with renal insufficiency. Such treatments, however, could be responsible for the appearance of unique abnormalities not seen prior to initiation of therapy, e.g., complications of dialysis. They could alter the disease process and create new disease conditions, e.g., loss of body weight, and premature atherosclerosis. Some symptoms resulting from impaired renal function may fail to respond fully to treatment, while others may even progress despite dialysis treatment.

As one can appreciate, there remains a need for additional options to the presently available treatments for renal dysfunctions, especially renal failure. In particular, there remains a need in the art to develop improved ways to treat renal dysfunctions, especially renal failure.

SUMMARY OF INVENTION

It is an object of the invention to provide a methods for inhibiting intraglomerular hypertension.

It is another object of the invention to provide a method for inhibiting glomerulosclerosis.

It is yet another object of the invention to provide a method for inhibiting glomerular-interstitial fibrosis.

It is still another object of the invention to provide a method for treating renal dysfunctions associated with intraglomerular hypertension, glomerulosclerosis or glomerular-interstitial fibrosis.

It is another object of the invention to provide a method for treating renal failure.

These and other objects of the invention are provided by one or more of the embodiments provided below.

In one embodiment of the invention there is provided a method for inhibiting intraglomerular hypertension, glomerulosclerosis, or glomerular-interstitial fibrosis, which comprises administering to a mammal in need of such treatment a therapeutically effective amount of a particular class of protein kinase C inhibitors.

In still another embodiment of the invention there is provided a method for treating renal dysfunctions associated with intraglomerular hypertension, glomerulosclerosis, or glomerular-interstitial fibrosis, which comprises administering to a mammal in need of such treatment a therapeutically effective amount of the protein kinase C inhibitor.

In still yet another embodiment of the invention there is provided a method for treating renal failure which comprises administering to a mammal in need of such treatment a therapeutically effective amount of the protein kinase C inhibitor.

The present invention identifies compounds which are effective in treating renal dysfunctions, especially renal dysfunctions associated with intraglomerular hypertension, glomerulosclerosis, or glomerular-interstitial fibrosis in humans.

DETAILED DESCRIPTION OF THE INVENTION

It is a discovery of the present invention that the therapeutic use of a particular class of protein kinase C inhibitors, i. e., inhibitors of the P isozyme of protein kinase C, and especially P isozyme selective inhibitors of PKC, inhibits intraglomerular hypertension, glomerulosclerosis, and glomerular-interstitial fibrosis, and especially such events associated with renal dysfunctions. Consequently, such compounds can be used therapeutically to treat renal dysfunctions, especially renal dysfunctions associated with intraglomerular hypertension and/or hyperfiltration, e.g., renal insufficiency, acute and chronic renal failure, and complications associated with loss of renal function. The compounds can also be used prophylactively to prevent the onset of renal dysfunctions.

The method of this invention preferably utilizes those protein kinase C inhibitors that effectively inhibit the P isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and 5,057,614, all incorporated by reference herein. Macrocyclic bis-indolylmaleimides are particularly represented by the compounds of formula 1. These compounds, and methods for their preparation, have been disclosed in U.S. Pat. No. 5,552,396, which is incorporated herein by reference. These compounds are administered in a therapeutically effective amount to a human to inhibit intraglomerular hypertension, glomerulosclerosis, and glomerular-interstitial fibrosis, or to treat renal dysfunctions. These compounds can also be administered to patients at risk of the disease conditions mentioned above as prophylactics.

One preferred class of compounds for use in the method of the invention has the formula (I):

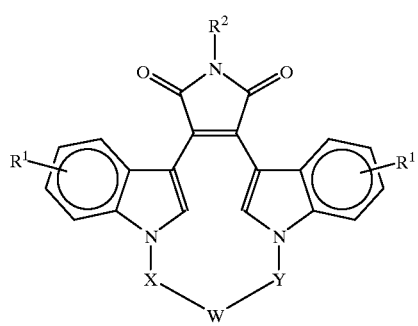

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, —NR$^4$R$^5$, or —NHCO(C$_1$–C$_4$ alkyl);

R$^2$ is hydrogen, CH$_3$CO—, —NH$_2$, or hydroxy;

R$^3$ is hydrogen, —(CH$_2$)$_m$aryl, -C$_1$–C$_4$ alkyl, —COO(C$_1$–C$_4$ alkyl), —CONR$^4$R$^5$, —(C=NH)NH$_2$, —SO(C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine with the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein R$^1$ and R$^2$ are hydrogen; and W is a substituted alkylene, —O—, S—, —CONH—, —NHCO— or —NR$^3$—. Particularly preferred compounds for use in the invention are compounds of the formula Ia:

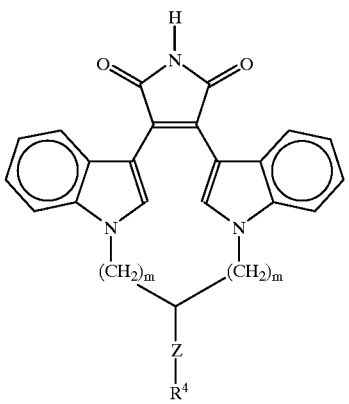

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$, or a pharmaceutically acceptable salt, prodrug or ester thereof.

Other preferred compounds for use in the method of the present invention are compounds wherein W in formula I is —O—, Y is a substituted alkylene, and X is an alkylene. These preferred compounds are represented by formula Ib:

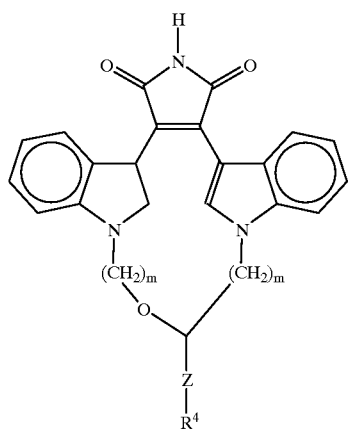

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. Nos. 5,552,396 and in Faul et al. EP publication 0 657 411 A1, all of which are incorporated herein by reference.

One particularly preferred protein kinase-β inhibitor for use in the method of this invention is the compound described in Example 5 g ((S)-3,4-[N, N'-1,1'-((2"-ethoxy)-3'"(O)-4'"-(N,N-dimethylamino)-butane)-bis-(3,3'-indolyl)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts, as described in U.S. Pat. No. 5,710,145 (incorporated herein by reference).

A preferred mesylate salt can be prepared by reacting a compound of the formula II:

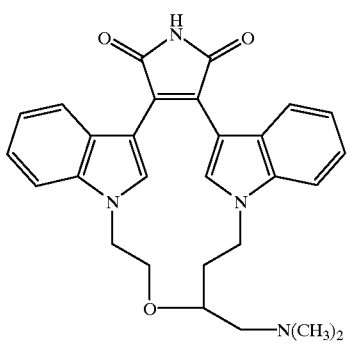

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1, The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours.

The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared in a crystalline form. The trihydrate form of the salt may be readily converted to the monohydrate upon drying or exposure to 20–60% relative humidity. The salt is substantially crystalline demonstrating a defined melting point, birefringence, and an X-ray diffraction pattern. Generally, the crystals have less than 10% amorphous solid and preferably less than 5% and most preferably less than 1% amorphous solid.

The mesylate salt is isolated by filtration or other separation techniques appreciated in the art, directly from the reaction mixture in yields ranging from 50% to 100%. Recrystallization and other purification techniques known in the art may be used to purify the salt further if desired.

Renal dysfunctions can be caused by a variety of conditions. Usually glomerular insult and injury leads to a compensatory increase in the filtration through the remaining functional glomeruli. This compensatory hyperfiltration response leads to intraglomerular hypertension in the remaining functional glomeruli. Chronic intraglomerular hypertension damages the remaining glomeruli in a fashion that is independent of the initial glomerular insult. Thus, while hyperfiltration of the remaining glomeruli is an attempt to maintain near normal renal function, it is maladaptive and leads to renal failure by a mechanism that is independent of the initial renal insult. Therefore, increases in glomerular pressure may be a final common denominator in the pathogenesis of chronic renal failure due to a variety of renal insults/injury, e.g., diabetes, glomerulonephritis, hypertension, obstructive nephropathies, etc.

Associated with the pathogenesis of chronic renal failure is a fibrotic reaction in the kidney which is manifested by glomeriilosclerosis and interstitial fibrosis. Although a variety of cytokines could be involved in this process, transforming growth factor-β, a potent inducer of extracellular matrix protein synthesis has been implicated in a variety of conditions associated with renal dysfunctions, especially chronic renal failure. Transforming growth factorβ inhibits the breakdown of the extracellular matrix.

Intraglomerular hemodynamic plays an important role in the pathogenesis of renal dysfunctions, e.g., chronic renal failure. There are several lines of evidence or observations to suggest that hyperfiltration causes continuing renal damage and renal failure via a hemodynamic mechanism. It has been noted that reduction in renal perfusion which leads to a decrease in glomerular pressure preserves renal function. Reduction in protein intake decreases glomerular filtration. In both preclinical models and in treatment of human diseases, low protein diets retard the progression of chronic renal failure. Angiotension converting enzyme (ACE) inhibitors have been shown to retard the progression of certain forms of chronic renal disease. It is believed that ACE inhibitors exert their renoprotective effects by reducing efferent glomerular arteriolar tone and thereby decreasing intraglomerular pressure. Therefore, treatments reducing or inhibiting intraglomerular pressure should retard or inhibit the progression of renal dysfunctions, e.g., chronic renal failure.

Though not wishing to be limited to any particular mechanism of action, applicants believe that mechanical increase in intraglomerular pressure leads to an increase in transforming growth factor-β expression through protein kinase C-β. Applicants have demonstrated that administration to diabetic rats of the PKC inhibitors described in the present invention normalizes the intraglomerular hypertension as well as the increased level of transforming growth factor-β.

The inhibitors of the β isozyme of PKC described in the present invention can be used to treat the disease conditions associated with intraglomerular hypertension, glomerulosclerosis, and glomerular-interstitial fibrosis, especially a variety of renal dysfunctions.

Renal dysfunctions treatable by the compounds of the present invention include those that are associated with intraglomerular hypertension and/or hyperfiltration, especially renal insufficiency, acute and chronic renal failure, and abnormalities and/or complications associated with loss of renal function. The compounds could also be used prophylactively before the onset of the manifestation of any renal dysfunctions to people at risk for potential loss of renal functions.

Loss of renal function includes acute and chronic renal failure. Acute renal failure is broadly defined as a rapid deterioration in renal function sufficient to result in accumulation of nitrogenous wastes in the body. The causes of such deterioration include renal hypoperfusion, obstructive uropathy, and intrinsic renal disease such as acute glomerulonephritis.

Chronic renal failure is usually caused by renal injuries of a more sustained nature which often lead to progressive destruction of nephron mass. Glomerulonephritis, tubulointerstitial diseases, diabetic nephropathy, and nephrosclerosis are among the most common causes of chronic renal failure.

The inexorably progressive course to renal failure is normally accompanied by failure of renal excretory function, severe malnutrition, impaired metabolism of carbohydrates, fats, and proteins, and defective utilization of energy. Uremia is the term generally applied to the clinical syndrome observed in patients suffering from profound loss of renal function. The presentation and severity of signs and symptoms of uremia often vary greatly from patient to patient, depending at least in part, on the magnitude of the reduction in functioning renal mass as well as the rapidity with which renal function is lost.

Renal failure can be divided into several stages. In the relatively early stage of chronic renal failure, glomerular filtration rate (GFR) is reduced but not to levels below about 35 to 50 percent of normal. Overall renal function is sufficient to maintain the patient symptom-free, although renal reserve may be diminished.

At a somewhat later stage in the course of clhonic renal failure, GFR is about 20 to 35 percent of normal. Azotemia occurs, and initial manifestations of renal insufficiency usually appear, with hypertension and anemia being the most common early abnormalities. Other derangements include carbohydrate intolerance, hyperuricemia, hypertriglyceridemia, and impaired ability to elaborate concentrated urine, the latter leading to polyuria and nocturia. Although patients are relatively asymptomatic at this stage, renal reserve is diminished sufficiently that any sudden stress, such as intercurrent infection, urinary tract obstruction, dehydration, or administration of a neplirotoxic drug, may compromise renal function still further, often leading to signs and symptoms of over uremia.

With further loss of nephron mass, i.e., a GFR below 20 to 25 percent of normal, the patient develops overt renal failure, which, in addition to increased severity of the anemia and hypertension, is characterized by metabolic acidosis, fluid overload, and various disturbances of the gastrointestinal, cardiovascular, and nervous systems.

One skilled in the art will recognize that a therapeutically effective amount of the protein kinase C inhibitor of the present invention is the amount sufficient to inhibit intraglomerular hypertension, glomerulosclerosis, or glomerular-interstitial fibrosis or the amount sufficient to retard or reverse the progression of renal dysfunctions. Such amount varies inter alia, depending upon the concentration of the compound in the therapeutic formulation, the body weight of the patient, the condition of the patient, and the method of application.

Generally, an amount of protein kinase C inhibitor to be administered as a therapeutic agent will be determined on a case by case basis by the attending physician. As a guideline, the degree of the renal insufficiency, the duration of the renal dysfunctions and its association with other diseases, e.g., diabetes, the body weight and the age of a patient, the mode of administration, and the like will be considered when setting an appropriate dose.

Generally, a suitable dose is one that results in a concentration of the protein kinase C inhibitor in the kidney at the range of 0.5 nM to 200 μM, and more usually between about 0.5 nM to 200 nM. It is expected that serum concentrations of 0.5 nM to 20 nM should be sufficient in many circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor should be needed. As noted above, the above amounts may vary on a case-by-case basis.

The therapeutic effects of the methods in the present invention can be evaluated by examining the effects of the PKC isozyme selective inhibitors on cultured mesangial cells. Specifically, the effects of the compounds of formula I and the preferred compounds of formula Ia and Ib on the mechanic pressure induced increases in transforming growth factor-β mRNA, protein expression or activity could be examined, An inhibition of stretch dependent increases in transforming growth factor-β is predictive of a positive response in treatment of renal dysfunctions. The effects of the compounds on renal dysfunctions could also be determined by assessing the glomerular filtration rate (GFR). A reduction or inhibition of a GFR increase induced by a high protein diet would also be predictive of a beneficial effect in treatment of renal dysfunctions.

Preclinical studies of animal models could also be used to evaluate the therapeutic effects of the compounds described in the present invention. Renal function can be measured upon administration of the compounds to animals who have undergone a partial nephrectomy, e.g., ⅞ this nephrectomy. A positive response is predictive of beneficial effects of the compounds in the treatment of renal dysfunctions associated with and/or derived from intraglomerular hypertension. Renal function can be monitored by serum creatinine level. The level of glomerulosclerosis, mesangial expansion and/or interstitial fibrosis can be monitored by renal histologic analysis.

The compounds of formula I, and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybeizoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 5–15 mg of the active ingredient.

However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels. In a preferred embodiment, intracavernosal injection of the compound directly to the smooth muscle is used.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon concentration of compound in the formulation. Generally, the formulation will be applied to the effected tissue in an amount affording from about 1 to about 500 $\mu$g compound per cm$^2$ of an affected tissue. Preferably, the applied amount of compound will range from about 30 to about 300 $\mu$g/cm$^2$, more preferably, from about 50 to about 200 $\mu$g/cm$^2$, and, most preferably, from about 60 to about 100 $\mu$g/cm$^2$.

The following formulation examples are illustrative only and are not intended to limit the scope of the invention in any way.

FORMULATION 1

Hard gelatin capsules are prepared using the following ingredients:

|  | Quantity (mg/capsule) |
| --- | --- |
| Active agent | 5 |
| starch, dried | 200 |
| magnesium stearate | 10 |
| Total | 215 mg |

The above ingredients are mixed and filled into hard gelatin capsules in 460 mg quantities.

FORMULATION 2

A tablet is prepared using the ingredients below:

|  | Quantity (mg/capsule) |
| --- | --- |
| Active agent | 15 |
| cellulose, microcrystalline | 10 |

-continued

| | Quantity (mg/capsule) |
|---|---|
| silicon dioxide, fumed | 10 |
| stearic acid | 5 |
| Total | 40 mg |

The components are blended and compressed to form tablets each weighing 665 mg.

FORMULATION 3

Tablets each containing 60 mg of active ingredient are made as follows:

| | Quantity (mg/tablet) |
|---|---|
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

What is claimed is:

1. A method for inhibiting intraglomerular hypertension, glomenruosclerosis, or glomerular-interstitial fibrosis in a non-diabetic mammal, which comprises administerinig to a non-diabetic mammal in need thereof a therapeutically effective amount of an inhibitor of the β isozyme of protein kinase C.

2. The method of claim 1 wherein the inhibitor of the β isozyme of protein kinase C is a bis-indolylmaleimide or a macrocyclic bis-indolylmaleimide.

3. The method of claim 1 wherein the inhibitor is β-isozyme selective and where the isozyme selectivity is selected from the group consisting of beta-1 and beta-2 isozymes.

4. The method of claim 3 wherein the protein kinase C inhibitor has the following formula:

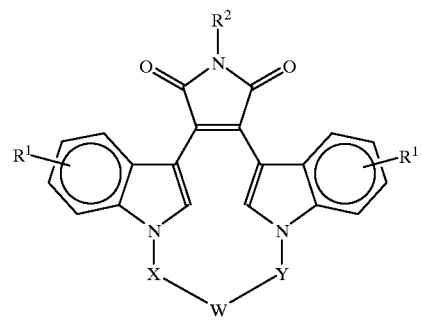

(I)

wherein:
W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy;

R$^3$ is hydrogen, —(CH$_2$)$_m$aryl, -C$_1$–C$_4$ alkyl, —COO (C$_1$–C$_4$ alkyl), —CONR$^4$R$^5$, —(C=NH)NH$_2$, —SO (C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

5. The method of claim 4 wherein the protein kinase C inhibitor has the following formula:

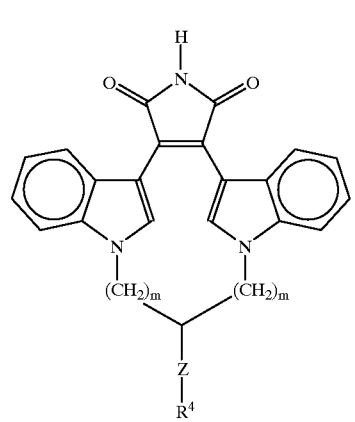

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3 or a pharmaceutically acceptable salt, prodrug or ester thereof.

6. The method of claim 4 wherein the protein kinase C inhibitor has the following formula:

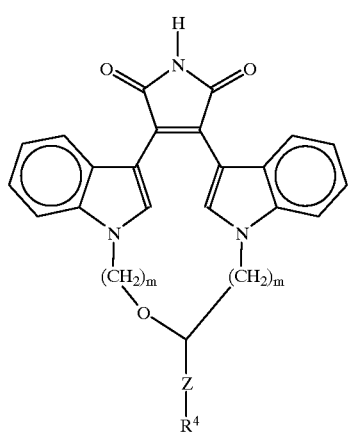

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

7. The method of claim 4, wherein the protein kinase C inhibitor comprises (S)-3,4-[N, N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

8. A method for treating a renal dysfunction associated with intraglomerular hypertension, glomerulosclerosis, or glomerular-interstitial fibrosis in a non-diabetic mammal, which comprises administering to a non-diabetic mammal in need thereof a therapeutically effective amount of an inhibitor of the β isozyme of protein kinase C.

9. The method of claim 8 wherein the inhibitor of the β isozyme of protein kinase C is a bis-indolylmaleimide or a macrocyclic bis-indolylmaleimide.

10. The method of claim 8 wherein the inhibitor is β-isozyme selective and where the isozyme selectivity is selected from the group consisting of beta-1 and beta-2 isozymes.

11. The method of claim 10 wherein the protein kinase C inhibitor has the following formula:

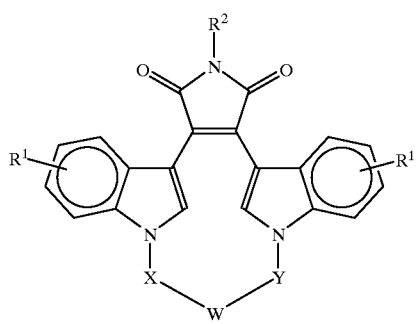

(I)

wherein:
W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -hetcrocycle-(CH$_2$)$_m$O, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy;

R$^3$ is hydrogen, —(CH$_2$)$_m$aryl, -C$_1$–C$_4$ alkyl, —COO (C$_1$–C$_4$ alkyl), —CONR$^4$R$^5$, —(C=NH)NH$_2$, —SO (C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

12. The method of claim 11 wherein the protein kinase C inhibitor has the following formula:

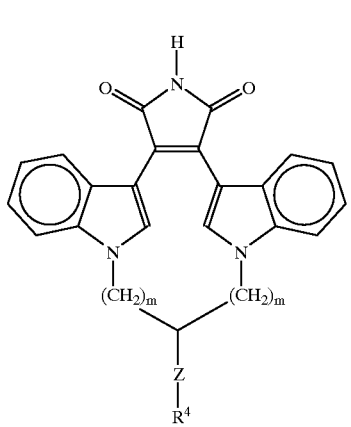

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$_5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof.

13. The method of claim 11 wherein the protein kinase C inhibitor has the following formula:

(Ib)

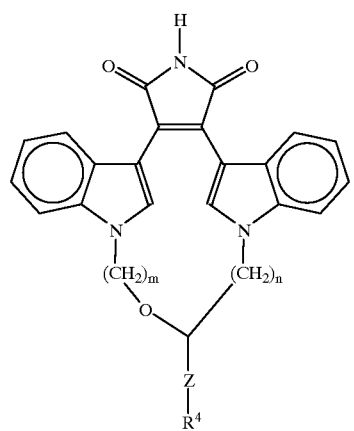

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

14. The method of claim 11, wherein the protein kinase C inhibitor comprises (S)-3,4-[N,N'-1,1'-((2''-ethoxy)-3'''(O)-4'''-(N,N-dimethylamino)-butane)-bis-(3,3'-indolyl)]-1(H)-pyrrole-2,5-dione or its pharmaceutically acceptable acid salt.

15. The method of claim 8 wherein the renal dysfunction is selected from the group consisting of renal insufficiency, acute renal failure, and chronic renal failure.

16. The method of claim 8 wherein the renal dysfunction is selected from the group consisting of acute renal failure and chronic renal failure.

17. The method of claim 16 wherein the acute renal failure is caused by renal hypoperfusion, obstructive uropathy, or intrinsic renal disease.

18. The method of claim 16 wherein the chronic renal failure is caused by glomerulonephritis, tubulointerstitial disease, or nephrosclerosis.

* * * * *